(12) United States Patent  (10) Patent No.: US 7,692,789 B1
Ebinger et al.  (45) Date of Patent: Apr. 6, 2010

(54) HIGH RESOLUTION ANALYSIS OF SOIL ELEMENTS WITH LASER-INDUCED BREAKDOWN

(75) Inventors: Michael H. Ebinger, Santa Fe, NM (US); Ronny D. Harris, Los Alamos, NM (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 416 days.

(21) Appl. No.: 11/734,948

(22) Filed: Apr. 13, 2007

(51) Int. Cl.
 *G01J 3/30* (2006.01)
(52) U.S. Cl. ..................................... 356/318
(58) Field of Classification Search ................ 356/318
 See application file for complete search history.

(56) References Cited

U.S. PATENT DOCUMENTS

| | | | |
|---|---|---|---|
| 4,616,134 A * | 10/1986 | Pruett et al. | 250/255 |
| 4,852,182 A * | 7/1989 | Herbin et al. | 382/109 |
| 5,847,825 A * | 12/1998 | Alexander | 356/318 |
| 6,657,721 B1 * | 12/2003 | Palleschi et al. | 356/318 |
| 7,092,083 B2 | 8/2006 | Chadwick et al. | |

OTHER PUBLICATIONS

Cremers et al. "Transportable laser-induced breakdown spectroscopy (LIBS) instrument for field-based soil analysis", Aug. 1996, SPIE vol. 2835, pp. 190-200.*

David A. Cremers, Michael H. Ebinger, David D. Breshears, Pat J. Unkefer, Susan A. Kammerdiener, Monty J. Ferris, Kathryn M. Catlett, and Joel R. Brown; Measuring Total Soil Carbon With Laser-Induced Breakdown Spectroscopy (LIBS); J. Environ. Qual., vol. 30; pp. 2202-2206; (Nov.-Dec. 2001).
"Spectrometer"; http://en.wikipedia.org/wiki/Spectrometer; (3 pages), 2007.
Ronny D. Harris, David A. Cremers, Michael H. Ebinger, and Brian K. Bluhm; "Determination of Nitrogen in Sand Using Laser-Induced Breakdown Spectroscopy"; Applied Spectroscopy; vol. 58; No. 7; pp. 770-775; (2004).
"Laser Induced Breakdown Spectroscopy"; http://en.wikipedia.org/wiki/Laser_induced_breakdown_spectroscopy; (4 pages), 2007.
"Partial Least Squares Regression"; http://users.aber.ac.uk/auj/talks/depttalk96/plsr.html; (1 page), 2007.

(Continued)

*Primary Examiner*—Kara E Geisel
(74) *Attorney, Agent, or Firm*—Thomas S. O'Dwyer; James Durkis; Paul A. Gottlieb

(57) ABSTRACT

The invention is a system and method of detecting a concentration of an element in a soil sample wherein an opening or slot is formed in a container that supports a soil sample that was extracted from the ground whereupon at least a length of the soil sample is exposed via the opening. At each of a plurality of points along the exposed length thereof, the soil sample is ablated whereupon a plasma is formed that emits light characteristic of the elemental composition of the ablated soil sample. Each instance of emitted light is separated according to its wavelength and for at least one of the wavelengths a corresponding data value related to the intensity of the light is determined. As a function of each data value a concentration of an element at the corresponding point along the length of the soil core sample is determined.

19 Claims, 2 Drawing Sheets

OTHER PUBLICATIONS

"Principle Components Regression"; http://users.aber.ac.uk/auj/talks/depttalk96/pcr.html; (2 pages), 2007.

"Regression Analysis"; http://en.wikipeida.org/wiki/Regression_analysis; (7 pages), 2007.

Michael H. Ebinger, M. Lee Norfleet, David D. Breshears, David A. Cremers, Monty J. Ferris, Pat J. Unkefer, Megan S. Lamb, Kelly J. Goddard, and Clifton W. Meyer; "Extending the Applicability of Laser-Induced Breakdown Spectroscopy for Total Soil Carbon Measurement"; Soil Sci. Soc. Am. J. 67; pp. 1616-1619; (2003).

"Partial Least Squares (PLS)"; http://www.statsoft.com/textbook/stpls.html; (14 pages), 1984.

P. Filzmoser; "Robust Principle Component Regression"; Dept. of Statistics, Prob. Theory, and Actuarial Maths.; Vienna University of Technology, Austria; (6 pages).

* cited by examiner

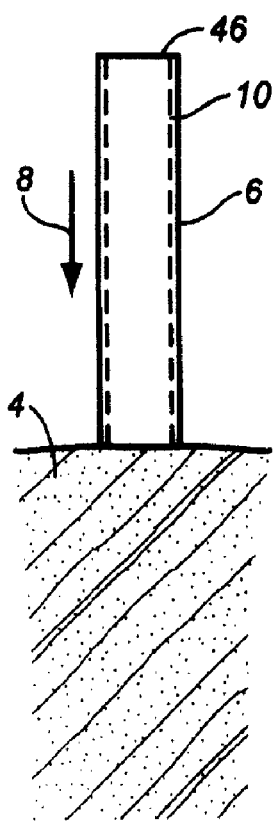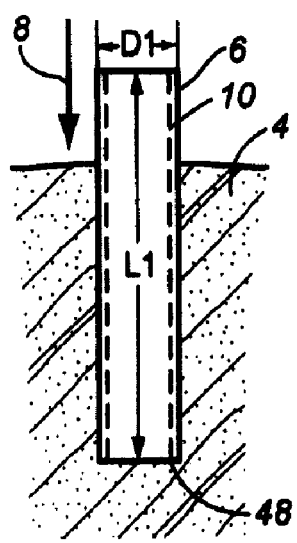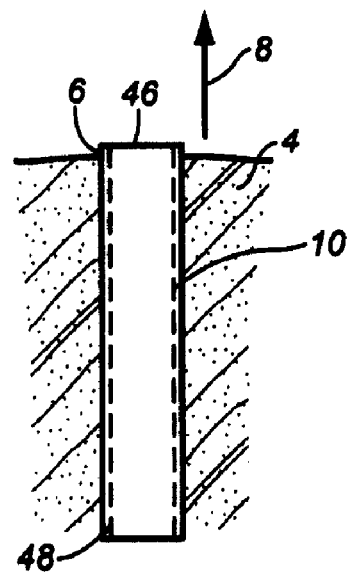
Fig. 1a  Fig. 1b  Fig. 1c

HIGH RESOLUTION ANALYSIS OF SOIL ELEMENTS WITH LASER-INDUCED BREAKDOWN

GOVERNMENT INTEREST

The United States has a paid-up license in the invention described and may manufacture and/or use this invention by or for the United States Government for governmental purposes in accordance with the terms of Contract Number W-7450-ENG-36.

BACKGROUND OF THE INVENTION

1. Field of the Invention

The present invention relates to analyzing soil core samples, and, more particularly, to analyzing soil core samples using laser-induced breakdown spectroscopy (LIBS).

2. Description of Related Art

Heretofore, no means existed for determining the concentration of an element at multiple locations of a soil core sample insitu. For example, heretofore, each section of a soil core sample was subjected to so-called dry combustion analysis to determine the concentration of an element in the sample. While dry combustion analysis has been deemed adequate in the past, presently there exists a need to accurately determine the concentration of an element, such as carbon, at multiple locations of a soil core sample to support national and international policies on carbon emissions and carbon trading in a more cost effective and timely manner than the prior art.

SUMMARY OF THE INVENTION

The invention is a laser-induced breakdown spectroscopy (LIBS) system for detecting a concentration of at least one element in a soil core sample. The system includes a carrier supporting a substantially vertically extracted soil core sample with a vertical section of the sample accessible via an opening in the carrier and a laser operative for outputting laser light along a path. Means are provided for supporting the carrier transverse to the path with the vertical section of the sample in the path. Means are provided for detecting light generated of at least one wavelength by a plasma produced in response to the laser light impinging on the sample and for outputting an electrical signal related thereto. Lastly, a controller is provided that is operative for controlling the laser to output at least one pulse of laser light for each step of the vertical section of the sample through the laser light path, for sampling in response to each pulse of laser light impinging on the sample the electrical signal output by the means for detecting, and for determining a concentration of at least one element in the soil core sample where the corresponding laser light pulse impinged as a function of each sampled electrical signal.

The means for detecting can include a fiber optic cable having a first end positioned to receive the light generated by the plasma and a second end for outputting said light; a spectrograph coupled to a second end of the fiber optic cable and operative for separating the light output thereby according to its wavelength; and a detector for detecting at least the wavelength of light corresponding to the element and for converting the detected wavelength of light into the electrical signal.

The controller can further be operative for converting each electrical signal output by the detector into an equivalent data value; comparing each equivalent data value to a plurality of reference data values determined from a like plurality of reference soil core samples that have different textures and/or compositions to determine an optimal fit of the equivalent data value to the reference data values; and determining the concentration of the element, e.g., carbon, in the soil sample based on said comparison.

Each reference data value can be determined by at least one of principal components regression (PCR) analysis and/or partial least squares regression (PLSR) analysis.

The means for supporting can include a moveable stage for supporting the carrier; and a drive coupled to the moveable stage and operative for moving the moveable stage at least one predetermined distance.

For each step of the vertical section of the sample through the laser light path, the controller can be operative for controlling the laser to output a plurality of laser light pulses to a location of the vertical section of the sample presently in the laser light path; determining a data value related to an average of a plurality of electrical signals output by the means for detecting in response to the output of said plurality of laser light pulses; and determining the concentration of at least one element in the soil core sample as a function of said data value.

For each step of the vertical section of the sample through the laser light path, the controller can be operative for converting each electrical signal output by the detector into equivalent data value, whereupon the data value determined by the controller is an average of a plurality of equivalent data values; comparing the data value to a plurality of reference data values determined from a like plurality of reference soil core samples that have different textures and/or compositions to determine an optimal fit of the data value to the reference data values; and determining the concentration of the element in the soil sample based on said comparison.

Each reference data value can be determined by at least one of principal components regression (PCR) analysis and/or partial least squares regression (PLSR) analysis on a corresponding reference soil sample.

The controller can further be operative for determining an integral of the concentration of the at least one element over a length of the vertical section of the sample.

The carrier can be tube-shaped. The opening can be a slot in the body of the tube that extends substantially parallel to a longitudinal axis of the tube.

The invention is also a method of detecting a concentration of at least one element in a soil core sample comprising: (a) using a container to extract an intact soil core sample from the ground; (b) forming at least one opening in said container whereupon at least a length of the intact soil core sample is exposed through said opening; (c) at each of a plurality of points along the length of the exposed soil core sample, ablating the soil core sample whereupon a plasma is formed that emits light characteristic of the elemental composition of the ablated soil core sample at said point; (d) separating each instance of emitted light according to its wavelength; (e) determining for at least one wavelength of each instance of emitted light a corresponding data value related to the intensity thereof; and (f) determining as a function of each data value a concentration of at least one element at the corresponding point along the length of the soil core sample.

Step (f) can include comparing the data value to a plurality of reference data values determined from a like plurality of reference soil core samples that have different textures and/or compositions to determine an optimal fit of the data value to the reference data values; and determining as a function of said comparison, a concentration of at least one element at the corresponding point along the length of the soil core sample.

Step (c) can include ablating the soil core sample a plurality of times at each point. Step (f) can include determining the concentration of the one element at each point as a function of an average of a plurality of the data values determined from ablation occurring at said point.

The method can further include determining as a function of data values determined for a subset of the length of the exposed soil core sample an integral of the concentration of the at least one element over said subset of the length.

The container can be a tube. The opening can be a slot in a wall of the tube that extends substantially parallel to an axis of the tube. The length of the soil core sample exposed in the slot can be in a depth direction of the soil core sample.

Lastly, the invention is a system for detecting a concentration of at least one element in a soil core sample. The system includes means for forming at least one opening in a container containing an intact soil core sample extracted from the ground whereupon at least a length of the intact soil core sample is exposed via said opening; means for ablating the soil core sample at each of a plurality of points along the length of the exposed soil core sample, whereupon, for each instance of ablating the soil core sample, an instance of a plasma is formed that emits an instance of light characteristic of the elemental composition of the corresponding ablated soil core sample; means for separating each instance of emitted light according to its wavelength; means for determining for at least one wavelength of each instance of emitted light a corresponding data value related to the intensity thereof; and means for determining as a function of each data value a concentration of at least one element at the corresponding point along the length of the soil core sample.

The system can further include means for comparing the data value to a plurality of reference data values determined from a like plurality of reference soil core samples that have different textures and/or compositions to determine an optimal fit of the data value to the reference data values; and means for determining as a function of said comparison a concentration of at least one element at the corresponding point along the length of the soil core sample.

The means for ablating can ablate the soil core sample a plurality of times at each point. The means for determining can determine the concentration of the one element at each point based an average of a plurality of the data values determined from the plurality of ablations occurring at said point.

The system can further include means for determining, as a function of data values determined for a subset of the length of the exposed soil core sample, an integral of the concentration of the at least one element over said subset of the length.

Specifically, an Nd:YAG laser operating at a wavelength of 1,064 nanometers (50 mJ pulses of 10 nanoseconds) is focused with a lens of 50 mm focal length on each of a plurality of portions of a soil core sample. Each instance of light emitted by a plasma in response to interaction between laser light output by the laser and the soil core sample is collected through a fused silica fiber optic cable pointed at the plasma from a distance of about 50 mm. A spectrograph having a 0.5 meter focal length resolves the detected laser light using a gated-intensified photo diode array detector.

A stepping motor and moveable stage coupled to transport an intact soil core sample through the focal point of the laser light allowed collection of spectra each 1 mm along the length (or depth) of the soil core sample. In one embodiment, twenty plasma light samples were collected and averaged at each step. Peak areas were integrated to estimate signal intensities for each spectrum, background signal was subtracted, and the carbon signal was ratioed to a signal of silicon at 251 nanometers wavelength to minimize sample-to-sample instrument variation. Typical measurement volumes for the analysis were between one and five $mm^3$.

Each intact soil core sample was collected in a plastic tube. A slit of approximately 10 mm was cut in the plastic tube along the length thereof to allow laser light access to the soil core sample. The soil core sample was then cycled through the instrument and data were collected at each 1 mm step along the core.

Carbon peak areas were estimated from the raw data and plotted with core depth. The data were then integrated by 2.5 cm depth and the geometric mean of the measurement computed for each interval. Comparison of data acquired in accordance with the present invention to dry combustion data was reasonably consistent.

BRIEF DESCRIPTION OF THE DRAWINGS

FIGS. 1(a)-1(c) are cross sectional side views of ground showing the progressive insertion there into of an insertion tool utilized to withdraw a soil core sample therefrom;

DETAILED DESCRIPTION OF THE INVENTION

Figure 2:
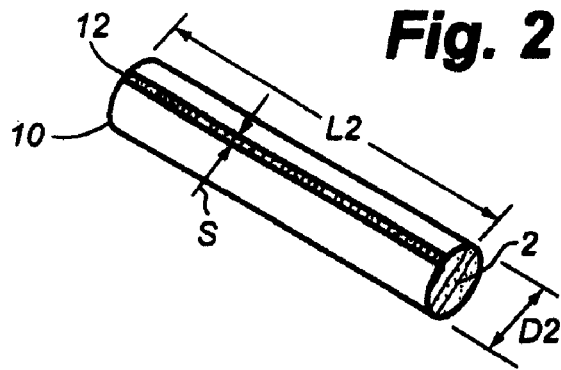
FIG. 2 is a perspective view of a soil core sample received in a carrier having a slot formed therein along the length thereof, wherein said carrier is positioned inside the insertion tool shown in FIGS. 1(a)-1(c) during removal of the soil core sample.

The present invention will be described with reference to the accompanying figures where like reference numbers correspond to like elements.

With reference to FIGS. 1(a)-1(c) and 2, a soil core sample 2 is extracted from the earth or ground 4 via any suitable coring apparatus, such as, without limitation, a so-called Giddings probe or a core from shallow drill-rig operations. More specifically, an insertion tool 6 having a carrier or container 10 (shown in phantom in FIGS. 1(a)-1(c)) received therein is inserted to ground 4 substantially vertically in the direction shown by arrows 8 in FIGS. 1(a) and 1(b). Once carrier 10 has acquired a suitable vertical depth of soil core sample 2, insertion tool 6 is vertically extracted from ground 4 in the direction shown by arrow 8 in FIG. 1(c).

Insertion tool 6 can be any suitable and/or desirable length L1 and diameter D1, such as, without limitation, L1=3 ft. and diameter D1=1 in. Insertion tool 6 is typically made of a tough durable metal, such as aluminum, an aluminum alloy, steel, a steel alloy, etc. The foregoing dimensions and material selection for insertion tool 6, however, are not to be construed as limiting the invention since it is envisioned that an insertion tool having any suitable and/or desirable dimensions and made of any suitable and/or desirable material can be utilized.

Once insertion tool 6 has been removed from ground 4, carrier 10 is removed therefrom. Carrier 10 can have a length L2 which can be approximately the same as length L1 and diameter D2 which is smaller than diameter D1. However, this is not to be construed as limiting the invention.

Desirably, carrier 10 is made from a material that is rigid but can readily be cut to facilitate access to at least a length of soil core sample 2 along its depth direction, i.e., the direction soil core sample 2 was extracted from ground 4. One suitable, non-limiting material that carrier 10 can be made from includes any suitable and/or desirable form of plastic. Desirably, insertion tool 6 and/or carrier 10 are tube shaped. However, this is not to be construed as limiting the invention since any suitable and/or desirable shape of insertion tool 6 and/or carrier 10 can be utilized.

At a suitable time after carrier 10, including intact soil core sample 2, has been removed from insertion tool 6, an opening 12, such as, an elongated slit, is formed in the body of carrier 10 parallel to the longitudinal axis thereof. Opening 12 can extend all or part of the length of carrier 10 as desired. Accordingly, the illustration in FIG. 2 of opening 12 running the entire length of carrier 10 is not to be construed as limiting the invention. In one desirable embodiment, opening 12 has a width S of approximately 10 mm. However, this is not to be construed as limiting the invention.

Opening 12 can be formed in any suitable or desirable manner, such as, without limitation, routing. However, this is not to be construed as limiting the invention.

Figure 3:
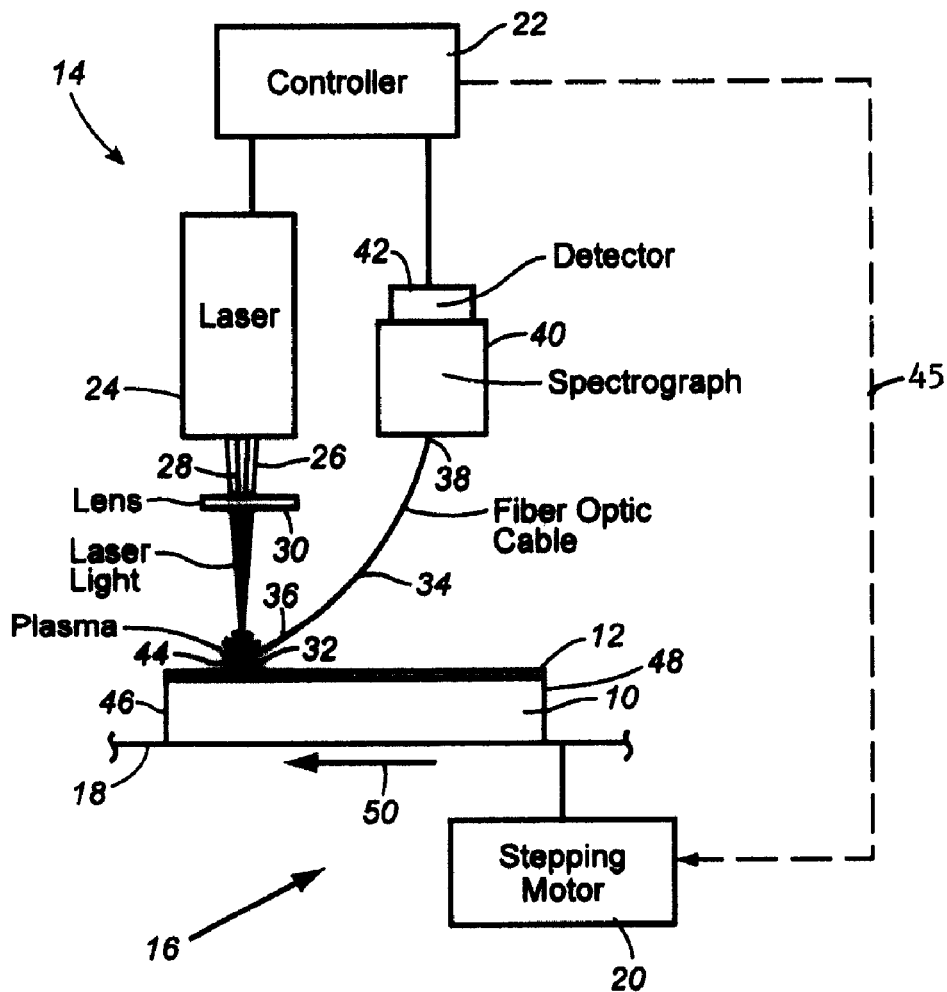
FIG. 3 is a diagrammatic view of a system for detecting a concentration of at least one element in the soil core sample in accordance with the present invention.

With reference to FIG. 3 and with continuing reference to FIG. 2, a laser-induced breakdown spectroscopy (LIBS) instrument 14 is utilized for testing soil core sample 2 in carrier 10. More specifically, a means for supporting 16 is utilized to support carrier 10 relative to LIBS instrument 14. Desirably, means for supporting 16 includes a moveable stage 18 which is moveable under the control of a motor 20, such as a stepping motor, operated either manually or under the control of a controller 22 of LIBS instrument 14.

In addition to controller 22, LIBS instrument 14 includes a laser 24 operating under the control of controller 22 for outputting laser light 26 along a path 28.

LIBS instrument 14 includes a lens 30 for focusing laser light 26 to a focal point 32 where the combination of carrier 10 supported by moveable stage 18 supports intact soil core sample 2 exposed via opening 12 in carrier 10. Thus, focal point 32 of laser light 26 impinges a point on the side surface of soil core sample 2 exposed through opening 12 and carrier 10.

LIBS instrument 14 includes a fiber optic cable 34 having a first end 36 positioned to receive light generated by a plasma (discussed in greater detail hereinafter) generated in response to the interaction of focal point 32 of laser light 26 and the point of soil core sample 2 where said focal point 32 impinges. In one non-limiting embodiment, first end 36 is positioned about 50 mm away from the plasma. However, this is not to be construed as limiting the invention.

Fiber optic cable 34 includes a second end 38 which outputs into a spectrograph 40 light received from the plasma in first end 36. Spectrograph 40 is a well-known means for separating light output at second end 38 of fiber optic cable 34 according to its wavelength.

A detector 42 is positioned to detect at least one wavelength of emitted light separated by spectrograph 40 from the light output from second end 38 of fiber optic cable 34. Since each element outputs light at one or more wavelengths, detector 42 detecting at least one wavelength of light output by spectrograph 40 enables determination of an element in the plasma generated in response to laser light 26 impinging on a point of soil core sample 2. In one non-limiting embodiment, detector 42 can be a gated-intensified photodiode array. However, this is not to be construed as limiting the invention.

Detector 42 converts light at least one wavelength into a corresponding electrical signal which is supplied to controller 22. In response to receiving this electrical signal, controller 22 converts the electrical signal output by detector 42 into a corresponding digital data value related to amplitude of the electrical signal and, hence, the intensity of the light at least at the one wavelength being monitored. For example, when ablated by laser light 26, the element carbon produces a plasma 44 that emits light at, among other things, a wavelength of 247.8 nm. The combination of spectrograph 40 and detector 42 can be operative for detecting light at this wavelength while controller 22 can be operative for determining a corresponding data value related to the intensity of the light at this wavelength.

Desirably, laser 24 is an Nd:YAG laser having a wavelength of 1,064 nm, lens 30 has a focal length of 50 mm, and fiber optic cable 34 is a fused silica fiber optic cable.

The operation of LIBS instrument 14 and means for supporting 16 will now be described.

In operation, stepping motor 20 is controlled, either manually or via controller 22 (as indicated by dashed line 45) to step stage 18, and, hence, carrier 10 in the direction shown by arrow 50 transverse to path 28 of laser light 26. More specifically, means for supporting 16 translates opening 12 of carrier 10 transverse, desirably perpendicular, to path 28 of laser light 26 whereupon as carrier 10 is translated, path 28 of laser light 26 passes through opening 12 whereupon laser light 26 can interact with soil core sample 2 exposed via opening 12 in carrier 10 anywhere along the length of opening 12.

In operation, carrier 10 is initially positioned on moveable stage 18 such that focal point 32 impinges soil core sample 2 exposed via opening 12 in carrier 10 adjacent a first end 46 thereof. At a suitable time, controller 22 causes laser 24 to output laser light 26. In one non-limiting example, laser 24 outputs a 50 ml pulse of 10 nanosecond duration. However, this is not to be construed as limiting the invention.

In response to focal point 32 of laser light 26 impinging on soil core sample 2, soil core sample 2 is ablated thereby producing a plasma 44 that emits light that is detected by spectrograph 40 via fiber optic cable 34. Detector 42 detects one or more wavelengths of light output by spectrograph 40 and outputs one or more electrical signals indicative of each wavelength of light to controller 22 which converts each electrical signal into a corresponding data value related to the amplitude of the electrical signal and, hence, the intensity of the wavelength of emitted light. The processing of this data value will be described in greater detail hereinafter.

Next, means for supporting 16 steps carrier 10 a predetermined distance in direction 50. Thereafter, the process of causing laser light 26 to ablate a small sample of soil core sample 2 exposed via opening 12 of carrier 10 to create a corresponding plasma 44, and the acquisition by controller 22 of a data value related to the intensity of a desired wavelength of light emitted by plasma 44 is repeated in the manner described above. The process of means for supporting 16 stepping carrier 10 and the acquisition of a data value related to the intensity of at least one wavelength of light emitted by a corresponding plasma 44 is repeated until a desired length of soil sample 2, in its depth direction, has been sampled. Said process is continued until a desired number of readings are obtained or the second final end 48 of carrier 10 is reached.

At a suitable time, each data value corresponding to the intensity of light emitted by plasma 44 at least at one wavelength is compared to a plurality of reference data values determined from light acquired from a plurality of reference core samples that have different textures and/or compositions to determine an optimal fit of the data value to the reference data values. The concentration in the soil core sample 2 corresponding to the wavelength of light emitted by the plasma 44 is determined based on the comparison. Desirably, each reference data value is determined by either principle component regression analysis and/or partially least squares regression analysis on a corresponding reference soil sample in a manner known in the art. However, this is not to be construed as limiting the invention.

Once the concentration of the element in the soil core sample has been determined for each sample point or location along the length of opening 12, a plot of concentration of the element versus depth can be formed in any suitable and/or desirable manner, either manually or automatically via controller 22.

Desirably, instead of outputting a single pulse of laser light 26 at each sample point along the length of opening 12, a plurality of pulses of laser light can be output at each point and the resulting data values averaged to determine an average data value related to the electrical signals output by the detector 42 in response to the laser light pulses. In one non-limiting embodiment, twenty pulses of laser light 26 are output by laser 24 at each sample point along the length of opening 12. However, this is not to be construed as limiting the invention.

In order to avoid instrument variation between pulses of laser light 26 at each sample point of soil core sample 2, the data value corresponding the element being sampled, e.g., carbon, can be ratioed with a data value related to an element having a known wavelength, e.g., Si at 251 nm, to minimize such variation.

Also or alternatively, if desired, an integral of the concentration of the element, e.g., carbon, can be determined over a length of soil core sample 2 exposed via opening 12 of container 10. For example, if soil core sample 2 is ablated one or more times every 1 mm step along the length of opening 12 of container 10, the mathematical integral of the concentration of the least one element over a predetermined interval of the overall length, e.g., every 2.5 cm, can be determined and the geometric mean computed for each interval.

Reasonable agreement was found between the geometric means of the data values acquired utilizing the present invention for each 2.5 cm interval and dry combustion data obtained for said interval.

The present invention has been described with reference to the preferred embodiments. Obvious modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A system for detecting a concentration of at least one element in a soil core sample, said system comprising:
    a carrier supporting a substantially vertically extracted soil core sample with a vertical section of the sample accessible via an opening in the carrier;
    a laser operative for outputting laser light along a path;
    means for supporting the carrier transverse to the path with the vertical section of the sample in the path;
    means for detecting light generated according to its wavelength by a plasma produced in response to the laser light impinging on the sample and for outputting an electrical signal related thereto; and
    a controller operative for controlling the laser to output a plurality of laser light pulses for each step of the vertical section of the sample through the laser light path, for determining a data value related to an average of the plurality of electrical signals output by the means for detecting, and for determining a concentration of at least one element in the soil core sample where the corresponding plurality of laser light pulses impinged as a function of said data value.

2. The system of claim 1, wherein the means for detecting includes:
    a fiber optic cable having a first end positioned to receive the light generated by the plasma and a second end for outputting said light;
    a spectrograph coupled to a second end of the fiber optic cable and operative for separating the light output thereby according to its wavelength; and
    a detector for detecting at least the wavelength of light corresponding to the element and for converting the detected wavelength of light into the electrical signal.

3. The system of claim 2, wherein the controller is further operative for:
    converting each electrical signal output by the detector into an equivalent data value;
    comparing each equivalent data value to a plurality of reference data values determined from a like plurality of reference soil core samples that have different textures and/or compositions to determine an optimal fit of the equivalent data value to the reference data values; and
    determining the concentration of the element in the soil core sample based on said comparison.

4. The system of claim 3, wherein each reference data value is determined by at least one of principal components regression (PCR) and/or partial least squares regression (PLSR).

5. The system of claim 1, wherein the means for supporting includes:
    a moveable stage for supporting the carrier; and
    a motor coupled to the moveable stage and operative for stepping the moveable stage at least one predetermined distance.

6. The system of claim 1, wherein, for each step of the vertical section of the sample through the laser light path, the controller is operative for:
    converting each electrical signal output by the detector into equivalent data value, whereupon the data value determined by the controller is an average of a plurality of equivalent data values;
    comparing the data value to a plurality of reference data values determined from a like plurality of reference soil core samples that have different textures and/or compositions to determine an optimal fit of the data value to the reference data values; and
    determining the concentration of the element in the soil core sample based on said comparison.

7. The system of claim 6, wherein each reference data value is determined by at least one of principal components regression (PCR) analysis and/or partial least squares regression (PLSR) analysis on a corresponding reference soil core sample.

8. The system of claim 1, wherein the controller is further operative for determining an integral of the concentration of the at least one element over a length of the vertical section of the sample.

9. The system of claim 1, wherein:
    the carrier is tube-shaped; and
    the opening is a slot in the body of the tube that extents substantially parallel to a longitudinal axis of the tube.

10. A method of detecting a concentration of at least one element in a soil core sample comprising:
    (a) using a container to extract an intact soil core sample from the ground;
    (b) forming at least one opening in said container whereupon at least a length of the intact soil core sample is exposed through said opening;
    (c) at each of a plurality of points along the length of the exposed soil core sample, ablating the soil core sample whereupon a plasma is formed that emits light characteristic of the elemental composition of the ablated soil core sample at said point;

(d) separating each instance of emitted light according to its wavelength;

(e) determining for at least one wavelength of each instance of emitted light a corresponding data value related to the intensity thereof; and (f) determining as a function of each data value a concentration of at least one element at the corresponding point along the length of the soil core sample.

11. The method of claim 10, wherein step (f) includes:
comparing the data value to a plurality of reference data values determined from a like plurality of reference soil core samples that have different textures and/or compositions to determine an optimal fit of the data value to the reference data values; and
determining as a function of said comparison a concentration of at least one element at the corresponding point along the length of the soil core sample.

12. The method of claim 10, wherein:
step (c) includes ablating the soil core sample a plurality of times at each point; and
step (f) includes determining the concentration of the one element at each point as a function of an average of a plurality of the data values determined from ablation occurring at said point.

13. The method of claim 10, further including determining as a function of data values determined for a subset of the length of the exposed soil core sample an integral of the concentration of the at least one element over said subset of the length.

14. The method of claim 10, wherein:
the container is a tube;
the opening is a slot in a wall of the tube that extends substantially parallel to an axis of the tube; and
the length of the soil core sample exposed in the slot is in a depth direction of the soil core sample.

15. A system for detecting a concentration of at least one element in a soil core sample comprising:
means for forming at least one opening in a container containing an intact soil core sample extracted from the ground whereupon at least a length of the intact soil core sample is exposed via said opening;
means for ablating the soil core sample at each of a plurality of points along the length of the exposed soil core sample, whereupon, for each instance of ablating the soil core sample, an instance of a plasma is formed that emits an instance of light characteristic of the elemental composition of the corresponding ablated soil core sample;
means for separating each instance of emitted light according to its wavelength;
means for determining for at least one wavelength of each instance of emitted light a corresponding data value related to the intensity thereof; and
means for determining as a function of each data value a concentration of at least one element at the corresponding point along the length of the soil core sample.

16. The system of claim 15, further including:
means for comparing the data value to a plurality of reference data values determined from a like plurality of reference soil core samples that have different textures and/or compositions to determine an optimal fit of the data value to the reference data values; and
means for determining as a function of said comparison a concentration of at least one element at the corresponding point along the length of the soil core sample.

17. The system of claim 15, wherein:
the means for ablating ablates the soil core sample a plurality of times at each point; and
the means for determining determines the concentration of the one element at each point based on an average of a plurality of the data values determined from the plurality of ablations occurring at said point.

18. The system of claim 15, further including means for determining as a function of data values determined for a subset of the length of the exposed soil core sample an integral of the concentration of the at least one element over said subset of the length.

19. The system of claim 15, wherein:
the container is a tube;
the opening is a slot in a wall of the tube that extends substantially parallel to an axis of the tube; and
the length of the soil core sample exposed in the slot is in a depth direction of the soil core sample.

* * * * *